United States Patent [19]

Suzuki

[11] 4,384,149

[45] May 17, 1983

[54] PROCESS FOR THE PREPARATION OF 1-NITROALKENE

[75] Inventor: Shigeto Suzuki, San Francisco, Calif.

[73] Assignee: Chevron Research Company, San Francisco, Calif.

[21] Appl. No.: 280,427

[22] Filed: Jul. 6, 1981

[51] Int. Cl.[3] ................................................ C07B 11/00

[52] U.S. Cl. ...................................................... 568/943

[58] Field of Search ......................... 260/688; 568/943

[56] References Cited

U.S. PATENT DOCUMENTS 1,872,700 8/1932 Dreyfus .............................. 260/688

2,384,048 9/1945 Smith et al. ......................... 260/688

2,478,243 8/1949 Coe et al. ............................ 260/688

3,510,531 5/1970 Larkin et al. ....................... 568/943

FOREIGN PATENT DOCUMENTS 56-18943 7/1979 Japan .................................. 568/943

*Primary Examiner*—Paul F. Shaver

*Attorney, Agent, or Firm*—D. A. Newell; T. G. De Jonghe; C. J. Caroli

[57] ABSTRACT

A process for the preparation of 1-nitroalkene which comprises the reaction of a 1-alkene with dinitrogen tetroxide in the presence of oxygen and an ether solvent to form an alkene-dinitrogen tetroxide adduct and subsequent reaction of the resulting adduct with sodium fluoride in the presence of an inert gas.

8 Claims, No Drawings

PROCESS FOR THE PREPARATION OF 1-NITROALKENE

BACKGROUND OF THE INVENTION

This invention is concerned with an improved process for the preparation of 1-nitroalkene which comprises the reaction of a 1-alkene with dinitrogen tetroxide in the presence of oxygen and an ether solvent to form an alkene-dinitrogen tetroxide adduct and subsequent reaction of the resulting adduct with sodium fluoride in the presence of an inert gas.

The addition of dinitrogen tetroxide to olefins in ether solution is known to provide 1-nitro-olefins. Thus, 1-nitropropene has been prepared in the past by the reaction of propylene with dinitrogen tetroxide (N. Levy and C. W. Scaife, of the Chemical Society, Vol. 1946, pages 1093–1104). This reaction produces a mixture of compounds which include 1,2-dinitropropane, beta-nitroisopropyl nitrite and beta-nitroisopropyl nitrate. By hydrolyzing the beta-nitroisopropyl nitrite to beta-nitroisopropanol, making an ester of this alcohol, and finally, heating the ester, 1-nitro-1-propene may be obtained in about 15% to 20% yield based on the crude product. Higher yields of 1-nitro-olefin have been obtained from crude products resulting from the reaction of dinitrogen tetroxide with higher olefins, such as 1-octadecene and cyclooctene (W. K. Siefert, Journal of Organic Chemistry, Vol. 28, pages 125–129, 1963). This procedure involves treatment of the crude reaction product with an organic base, such as triethylamine, to obtain the desired nitroolefin. Ammonia has also been used in the elimination reaction, but with poorer yields.

1-Nitroalkenes are useful for the preparation of dialkylanilines as disclosed in my related copending application, Ser. No. 280,426, filed concurrently herewith. Dialkylanilines are useful intermediates for a variety of compounds having herbicidal and fungicidal activity.

SUMMARY OF THE INVENTION

It has now been found that 1-nitroalkenes containing 3–6 carbon atoms may be prepared in high yield by a process which comprises the steps of:

(a) contacting a 1-alkene having 3–6 carbon atoms with dinitrogen tetroxide in the presence of oxygen and an ether solvent at a temperature of from about −30° C. to about 70° C. to form an alkene-dinitrogen tetroxide adduct; and (b) contacting said adduct with sodium fluoride in the presence of an inert gas at a temperature of from about 150° C. to about 300° C.

Preferable 1-nitroalkenes prepared by this method include those containing 3–4 carbon atoms. Most preferably, the 1-nitroalkene is 1-nitropropene.

The 1-alkenes suitable for use in the process of the present invention may contain 3–6 carbon atoms, preferably 3 or 4 carbon atoms. Examples of suitable alkenes include 1-butene, 1-pentene and 1-hexene. An especially preferred 1-alkene is propylene.

The 1-alkene is generally reacted with dinitrogen tetroxide in an ether solution and in the presence of oxygen. Preferred solvents are aliphatic ethers, such as dialkyl ethers, wherein each alkyl group contains 2 to 8 carbon atoms, or saturated heterocyclic ethers containing 4 or 5 carbon atoms in the heterocyclic ring. Typical ethers include ethyl propyl ether, dioctyl ether, pentyl hexyl ether, tetrahydrofuran, tetrahydropyran, and the like. Most preferably, the solvent is diethylether. The reaction may be carried out at a temperature from about −30° C. to about 70° C., preferably from about −10° C. to about 30° C. The reaction pressure may be atmospheric, subatmospheric or superatmospheric. However, for convenience of conducting the reaction, the pressure is generally atmospheric. Generally, about 0.2 to 5 moles, and preferably about 0.5 to 2 moles, of dinitrogen tetroxide are utilized per mole of 1-alkene. The use of about 1 mole of dinitrogen tetroxide per mole of 1-alkene is especially preferred. The crude reaction product will usually contain a mixture of compounds, among which may include 1,2-dinitroalkane, beta-nitroalkyl nitrite, beta-nitroalkyl nitrate and beta-nitroalkanol. For purposes of convenience, the crude reaction product may be designated as the alkene-dinitrogen tetroxide adduct.

The crude alkene-dinitrogen tetroxide adduct thus formed is subjected to sodium fluoride catalyzed pyrolysis in the presence of an inert gas and without prior purification. Generally, this process is carried out by passing the adduct and the inert gas through a catalyst packed reactor. The adduct is passed into the reactor at an LHSV (Liquid Hourly Space Velocity) of from about 0.1 $hr^{-1}$ to about 10 $hr^{-1}$, and preferably from about 0.3 $hr^{-1}$ to about 3 $hr^{-1}$. The LHSV is calculated for standard conditions. The reaction may be carried out at a temperature from about 150° C. to about 300° C., preferably from about 180° C. to about 230° C. The inert gas may be any gas which is inert to the reaction, such as helium or argon. The preferred inert gas is nitrogen. The product is isolated and purified by conventional procedures such as extraction, distillation, chromatography, crystallization and the like.

The following examples are provided to illustrate the invention in accordance with the principles of this invention but are not to be construed as limiting the invention in any way except as indicated by the appended claims.

EXAMPLES

EXAMPLE 1

A Teflon reactor with a magnetic stirrer was charged with diethyl ether, 30 c.c., which was stirred under 1 atmospheric pressure of $O_2$ for 30 minutes at −60° C. Dinitrogen tetroxide, 8.8 g (0.096 mol), was added, and the temperature of the reaction mixture was raised to −10° C. With stirring and cooling, propylene gas 3.0 g (0.07 mol) was added in 30 minutes while the temperature of the reaction mixture fluctuated between −10° C. and +22° C. The stirring was continued at −10° C. for an additional 15 minutes. Excess dinitrogen tetroxide and ether were removed at 0° C. by stirring under 10 mmHg vacuum followed by blowing with a nitrogen stream at room temperature for 2 hours. In this manner, the propylene-$N_2O_4$ adduct as a yellow oil, 9.1 g (approximately 97% yield as the adduct), was obtained. The adduct did not show decomposition on standing at room temperature.

EXAMPLE 2

Sodium bifluoride tablets (Harshaw Chemical Co.) were crushed to 24–28 mesh size, and packed in a center section (4-inch length) of a 7-inch long SS-316 reactor tube (0.1415 inch I.D.) in a clam shell furnace. The packed catalyst bed was activated by heating at 400° C. for 2 hours under an $N_2$ stream to generate sodium fluoride. The 1:1 adduct of propylene and dinitrogen tetroxide was passed downward through the catalyst bed maintained at 200° C. and at 1 $hr^{-1}$ LHSV with a nitrogen stream at 600 $hr^{-1}$ VHSV. During the first hour, 1.2 g of the adduct was charged, and 0.73 g of organic liquid was collected in a trap at room temperature. The analysis of the liquid by a gas chromatogram (5% FFAP, the carrier gas) showed the liquid contained 2 wt. % unreacted adduct, 12 wt. % nitromethane, and 84 wt. % 1-nitropropene (about 86% selectivity). When the sodium fluoride bed temperature was raised to 300° C. (LHSV 1.5 $hr^{-1}$, the liquid product collected contained 8 wt. % unreacted adduct, 44 wt. % nitromethane and 38 wt. % 1-nitropropene (about 41% selectivity).

EXAMPLE 3

The same reactor as used in Example 2 was packed with a fresh sodium fluoride catalyst and preactivated at 400° C. for 1.5 hours under an $N_2$ stream. The propylene-dinitrogen tetroxide adduct was passed at 180° C. and 1 $hr^{-1}$ LHSV with a nitrogen stream at 600 $hr^{-1}$ VHSV. The liquid product was collected for 1 hour after the bed was onstream for one hour. 0.76 g liquid product was collected from 1.2 g feed. Analysis of the liquid product as before showed it to contain 59 wt. % unreacted adduct, 7 wt. % nitromethane, and 33 wt. % 1-nitropropene (about 81% selectivity). When the sodium fluoride bed temperature was raised to 200° C. (LHSV 1 $hr^{-1}$), the liquid product collected contained 22 wt. % unreacted adduct, 14% nitromethane and 59% 1-nitropropane (about 76% selectivity).

What is claimed is:

1. A process for the preparation of 1-nitroalkene having 3–6 carbon atoms which comprises the steps of:

(a) contacting a 1-alkene having 3–6 carbon atoms with dinitrogen tetroxide in the presence of oxygen and an ether solvent at a temperature of from about −30° C. to about 70° C. to form an alkene-dinitrogen tetroxide adduct; and (b) contacting said adduct with sodium fluoride in the presence of an inert gas at a temperature of from about 150° C. to about 300° C.

2. A process in accordance with claim 1, wherein said 1-alkene contains 3–4 carbon atoms.

3. A process in accordance with claim 1, wherein said 1-alkene is propylene.

4. A process in accordance with claim 1, wherein said ether solvent is diethylether.

5. A process in accordance with claim 1, wherein the reaction of the 1-alkene with dinitrogen tetroxide is carried out at a temperature of about −10° C. to about 30° C.

6. A process in accordance with claim 1, wherein the reaction of the alkene-dinitrogen tetroxide adduct with sodium fluoride is carried out at a temperature of about 180° C. to about 230° C.

7. A process in accordance with claim 1, wherein about 1 mole of dinitrogen tetroxide is employed per mole of 1-alkene.

8. A process in accordance with claim 1, wherein the inert gas is nitrogen.

* * * * *